(12) United States Patent
Mattejat

(10) Patent No.: US 9,651,486 B2
(45) Date of Patent: May 16, 2017

(54) METHOD AND DEVICE FOR MEASURING THE GAS CONTENT IN A LIQUID, AND USE OF SUCH A DEVICE

(71) Applicant: SIEMENS AKTIENGESELLSCHAFT, Munich (DE)

(72) Inventor: Arno Mattejat, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 197 days.

(21) Appl. No.: 14/422,723

(22) PCT Filed: Aug. 14, 2013

(86) PCT No.: PCT/EP2013/067000
§ 371 (c)(1),
(2) Date: Feb. 20, 2015

(87) PCT Pub. No.: WO2014/029675
PCT Pub. Date: Feb. 27, 2014

(65) Prior Publication Data
US 2015/0241344 A1    Aug. 27, 2015

(30) Foreign Application Priority Data
Aug. 21, 2012   (EP) .................................... 12181119

(51) Int. Cl.
*G01N 21/53*    (2006.01)
*G01N 29/02*    (2006.01)
*G01N 33/18*    (2006.01)

(52) U.S. Cl.
CPC ............ *G01N 21/532* (2013.01); *G01N 29/02* (2013.01); *G01N 33/18* (2013.01); *G01N 2201/062* (2013.01); *G01N 2291/02433* (2013.01)

(58) Field of Classification Search
CPC ...... G01N 21/532; G01N 29/02; G01N 33/18; G01N 2201/062; G01N 2291/02433
(Continued)

(56) References Cited
U.S. PATENT DOCUMENTS 4,681,601 A     7/1987 Foster
4,713,964 A *  12/1987 Ioannides ............ G01N 21/534
                                                            356/439
(Continued)

FOREIGN PATENT DOCUMENTS

DE          4400385 A1     7/1995
DE         10213076 B4     5/2014
GB          1085825 A     10/1967

*Primary Examiner* — Daniel S Larkin
(74) *Attorney, Agent, or Firm* — Laurence Greenberg; Werner Stemer; Ralph Locher

(57) ABSTRACT

The gas content of a liquid is quickly and reliably controlled by delivering at least one sub-quantity of the liquid into a measurement cell in which a negative pressure is set. A wave-shaped measurement signal is applied to the sub-quantity, and the wave-shaped measurement signal is measured by at least one detector after coming into contact with the sub-quantity of the liquid. A turbidity value of the liquid is determined and compared with a threshold. If the turbidity value is greater than or equal to the threshold, a pressure and a temperature in the measurement cell are measured, and the gas content in the liquid is ascertained using stored characteristics for the solubility of the gas in the liquid dependent on the pressure and temperature.

16 Claims, 2 Drawing Sheets

(58) Field of Classification Search
USPC .............. 73/19.01, 19.1, 19.05, 19.06, 19.11
See application file for complete search history.

(56) References Cited

U.S. PATENT DOCUMENTS

| | | | | |
|---|---|---|---|---|
| 5,072,595 | A * | 12/1991 | Barbier | F25B 41/006 |
| | | | | 250/577 |
| 5,153,175 | A * | 10/1992 | Krueger | C07K 14/60 |
| | | | | 514/11.2 |
| 5,243,848 | A * | 9/1993 | Cox | G01N 33/2841 |
| | | | | 73/19.05 |
| 5,635,631 | A | 6/1997 | Yesudas et al. | |
| 6,138,497 | A * | 10/2000 | Nix | G01N 7/14 |
| | | | | 250/339.13 |
| 6,803,594 | B2 * | 10/2004 | Spolaczyk | G01N 21/8507 |
| | | | | 250/574 |
| 7,559,223 | B2 * | 7/2009 | Chen | G01N 7/14 |
| | | | | 702/24 |
| 8,490,464 | B1 * | 7/2013 | Selby | G01N 7/14 |
| | | | | 73/19.1 |
| 2002/0144536 | A1 * | 10/2002 | Sullivan | G01N 33/34 |
| | | | | 73/19.05 |
| 2002/0194907 | A1 | 12/2002 | Bostrom et al. | |
| 2003/0029228 | A1 | 2/2003 | Bloder et al. | |
| 2003/0056568 | A1 | 3/2003 | Kleinberg et al. | |
| 2004/0206157 | A1 * | 10/2004 | Chen | G01N 7/16 |
| | | | | 73/19.05 |
| 2011/0093200 | A1 | 4/2011 | Hsu et al. | |
| 2011/0259090 | A1 | 10/2011 | Angelescu et al. | |
| 2012/0048808 | A1 * | 3/2012 | Zhou | C02F 5/10 |
| | | | | 210/696 |

\* cited by examiner

METHOD AND DEVICE FOR MEASURING THE GAS CONTENT IN A LIQUID, AND USE OF SUCH A DEVICE

BACKGROUND OF THE INVENTION

Field of the Invention

The invention relates to a method for measuring the gas content in a liquid. The invention further relates to a device for measuring the gas content in a liquid and to a use of such a device.

In many technical areas a measurement of the gas content in operational liquids is necessary, since the presence of gas influences the characteristics of these liquids. A measurement of the gas content is therefore relevant for example for the dimensioning and construction of machine parts and for development of liquids with favorable gas separation behavior. In particular it is important to know the gas content of a lubricating liquid or of a heating or cooling liquid.

The measurement of gas in liquids is of importance for example for the trouble-free operation of an electrochemical cell, such as e.g. a fuel cell. In operation of a fuel cell any heat losses arising must be largely removed from the active area of the fuel cell, in order to avoid local overheating (so-called "hot spots"). This is done most effectively by a liquid coolant which flows through the fuel cell.

In a fuel cell stack with fuel cells based on the Polymer-Electrolyte-Membrane (PEM) technology the electrodes on the side facing away from an electrolyte membrane or catalyzer layer come into contact in each case with a so-called bipolar plate or cooling unit. The task of the bipolar plate is to separate the individual fuel cells (on the media side), to take care of current flow in the cell stack and to remove the reaction heat.

In addition to conducting the current and conveying the reactants hydrogen and oxygen, the bipolar plates fulfill their cooling function by a coolant, especially water, being conveyed through said plates. Because of its high specific heat capacity, low electrical conductivity, good media compatibility and the low operating costs, de-ionized water (deionate) is used as a coolant in PEM-fuel cells. The coolant may only have a very low conductivity and should be as gas-free as possible, so that no gas bubbles adhere to the surface of the bipolar plates, since areas with gas bubbles are cooled less effectively and therefore will be locally overheated. Because of physical and constructional conditions however it cannot be excluded that even originally gas-free cooling water takes up gas during its use and is provided with bubbles.

In large heating systems so-called vacuum degassers are employed to remove dissolved air from the heating water. Similar devices can also be used in fuel cell systems to remove gas from the heating water. The aim of these methods is not to allow any two-phase mixture (gas/water) in the cooling water so that a gas accumulation, and thus a local overheating, cannot occur on the bipolar plate.

BRIEF SUMMARY OF THE INVENTION

The underlying object of the invention is to make possible rapid and reliable checking of the gas content of a liquid, e.g. of a coolant.

The object is achieved in accordance with the invention by a method for measuring a gas content in a liquid, wherein at least one sub-quantity of the liquid is conveyed into a measurement cell, a vacuum is set in the measurement cell, the sub-quantity has a wave-shaped measurement signal applied to it, the measurement signal is measured after coming into contact with the sub-quantity, a turbidity value of the liquid is determined and compared with a threshold, and if the turbidity value is greater than or equal to the threshold, a pressure and a temperature are measured in the measurement cell and the gas content in the liquid is determined on the basis of stored characteristic data for the solubility of the gas in the liquid as a function of pressure and temperature.

The object is further achieved in accordance with the invention by a device for measuring the gas content in a liquid comprising:

A measurement cell for receiving at least a sub-quantity of the liquid,

Means for generating a vacuum in the measurement cell,

A measurement signal transmitter for applying a wave-shaped measurement signal to the sub-quantity, At least one detector for measuring the measurement signal after it has come into contact with the sub-quantity in the measurement cell, Sensors for determining a pressure and a temperature in the measurement cell, And also an analysis and control unit which is configured to determine a turbidity value of the liquid and to compare said value with a threshold and, if the turbidity value is equal to or greater than the threshold, to determine the gas content in the liquid with the aid of characteristic data stored for the solubility of the gas in the liquid as a function of pressure and temperature.

The object is finally achieved in accordance with the invention by using such a device for measuring the gas content in a coolant of an electrochemical cell, especially a fuel cell.

The advantages and preferred embodiments given below for the method can be transferred analogously to the device and its use.

The invention is based on the knowledge that during the expansion of a liquid with dissolved gas, the gas occurs in the form of small bubbles, which lead to a turbidity of the liquid. Turbidity in this case is to be understood as a change of the transmission and the reflection of the sub-quantity for waves, which is caused by a change of the liquid/gas composition of the sub-quantity. Quantitatively this change is expressed by the turbidity value. To be able to determine whether gas is contained in liquid it is thus initially necessary to detect the turbidity of the liquid during the expansion of the liquid in the measurement cell. In addition sensors are necessary, with the aid of which the pressure and the temperature in the measurement cell are determined. The detected values for pressure and temperature at the onset of turbidity are compared in such cases with known solubility graphs in order to determine the quantity of gas in the liquid under the measured conditions. If for example the liquid involves water, the solubility of air and other gases in water as a function of pressure and temperature of the environment is already known per se. As an alternative characteristic data for the solubility of the gas dissolved in the liquid is experimentally detected and stored beforehand, which is employed later during measurement of the gas content in the corresponding liquid.

The measurement can thus briefly be summarized as follows: the pressure and the temperature in the measurement cell are regulated so that a detectable turbidity occurs and at the onset of the turbidity the quantity of gas is determined by the solubility data for the gas, wherein the pressure and temperature values at the onset of the turbidity are used for this purpose.

Comprehensive data collections and publications on the subject of solubility of a gas in water as a function of pressure and temperature exist, which are based on Henry's law for describing the solubility behavior of volatile substances in a liquid. A graphical presentation of the solubility of nitrogen in water as a function of the pressure and the temperature is to be found in FIG. B I-4.1 of the physicochemical data collection/R44 of Kraftwerk Union. A tabular summary of the solubility of different gases in water as a function of temperature is published in MESSER GRIESHEIM Gase-Handbuch (handbook of gases), table 29 on page 92, 1969 edition. A further graphical presentation of the solubility of air in water as a function of pressure and temperature is to be found in the Article entitled "Druckausdehnungsgefäße in Heizungsanlagen (pressure expansion vessels in heating systems)" by J Spang in German periodical IKZ-Haustechnik, Edition 4/1996, page 30 ff. FIG. 2.

The temperature and pressure values with which the comparison is made thus originate from sources that can be found for each gas in definitive works and tables (characteristic graphs for solubility of a gas as a function of temperature and pressure). Such sources disclose the maximum quantity of gas which can be dissolved at a specific temperature and a specific pressure. If the pressure falls below the value for the pressure at a constant temperature or if the temperature exceeds the value for the temperature at a constant pressure, the gas begins to escape from the solution as bubbles and thus becomes visible as turbidity.

Preferably the sub-quantity has an electromagnetic measurement signal applied to it. For this a light source as measurement signal transmitter and at least one light detector are provided. The measurement cell in such cases is transparent for the light of the light source.

As an alternative the sub-quantity preferably has an acoustic measurement signal, especially ultrasound, applied to it. In this case an ultrasound transmitter and an ultrasound detector are required.

The determined turbidity value represents a measure for the change of composition of the liquid with falling pressure. The turbidity value is especially determined continuously or at intervals of a few seconds up to a few hours and compared to a threshold. The threshold in this case defines the onset of the turbidity in the liquid. If in the measurement the turbidity value thus reaches the threshold or exceeds said threshold a turbidity of the liquid is detected which qualitatively indicates the presence of gas in the liquid.

To determine the gas content, the pressure and the temperature in the measurement cell are taken into account at the onset of turbidity. As a result of available characteristic data, the amount of dissolved gas can be deduced from the temperature and the pressure at which the turbidity occurs. For example an early onset of the turbidity at a pressure which is just below the ambient pressure indicates a large quantity of gas.

If gas is established during the measurement in particular a corresponding signal is output, which is forwarded to a control unit or to an optical display. With this signal a vacuum degasser in particular is switched on and is operated until such time as the liquid is gas-free again.

When the device is used for measuring a gas content in an electrochemical cell device, such as a fuel cell for example, the measurement cell in this case can be disposed on an ancillary or bypass line in parallel to a main line for the coolant circuit, so that only a small part of the coolant is conveyed through the measurement cell. As an alternative the measurement cell can be integrated into the main line so that it is not necessary to divert the coolant for measurement purposes.

The gas content can be monitored in the liquid discontinuously by a small sub-quantity being conveyed by a pump into the measurement cell from the main flow in the main line and after an inlet valve has been closed, by the pump being controlled in such a way that the pressure in the measurement cell drops slowly and the optical measurement is carried out.

However as an alternative the liquid is introduced continuously into the measurement cell for measuring the turbidity value. For this a regulation valve is preferably provided for continuous inflow of coolant into the measurement cell. For pressure reduction in the measurement cell the regulation valve is controlled such that the desired, temperature-dependent pressure values which are needed for the measurement are set at a constant pump speed. The pressure in the measurement cell drops slowly until a turbidity starts to occur. From the pressure and temperature measured at this point in time the gas load can be determined. The threshold for carrying out the method is a pressure just above the boiling pressure (appr. 50 mbar above the boiling pressure). Above this pressure threshold it can be established through the occurrence of the turbidity whether gas is contained in the liquid.

A fixed choke valve and a reduction of the pressure by the pump represent a further alternative. The evaluation is carried out as described in the above paragraph.

An advantage of the measurement described above is that the method works with small volumes or sub-quantities of liquid and minimal amounts of gas occurring, so that the measurement is characterized by a high sensitivity. A further advantage is that it can run fully automatically and without the intervention of an operator. If the gas content of a coolant for an electrochemical cell is measured, the tested sub-quantity is additionally not disposed of but is pumped back after the measurement of the turbidity especially into the coolant circuit of the electrochemical cell.

In accordance with a preferred embodiment the pressure and/or the temperature in the measurement cell are controlled so that they remain above the boiling point. The boiling point here is defined as a point at the liquid/gaseous phase boundary in the phase diagram (steam pressure curve) of the liquid, in which the saturation temperature or boiling temperature and the saturation pressure or boiling pressure is reached. Especially the pressure in the measurement cell is controlled so that during the measurement it remains at the corresponding temperature around 50 mbar above the boiling pressure. On reduction of the pressure in the measurement cell the liquid vaporizes in the form of small bubbles if the boiling pressure is reached at the corresponding temperature. Such steam bubbles have the same influence on the turbidity as a gas dissolved in the liquid. In order to avoid a corruption of the measurement results for the turbidity value because of boiling bubbles, the temperature and pressure sensors are needed, through the signals of which it can be distinguished whether the turbidity involves an effect of the escape of gas from or the vaporization of the liquid. Therefore there is provision, during the execution of the method, for the pressure and the temperature to be measured especially continuously or at short intervals in order to be able to react in good time to the boiling point being approached.

In accordance with a preferred variant the threshold is specified as a numerical value. In such cases the threshold can be a value stored in the analysis unit, but can however also be entered as a new value before each measurement.

In order to detect changes of the liquid which are not caused by the gas content in the sub-quantity, but which influence the transmission and reflection characteristics of the liquid however, e.g. colorations or contamination or changes to measurement components (for example by an attenuation of the light source), a light measurement to define a reference value is expediently carried out before the vacuum is set (i.e. still at system pressure. The reference value is obtained at the beginning when the pressure has not yet been reduced in the measurement cell, in particular via a light or ultrasound measurement, and defines an initial state of the liquid in respect of its turbidity. A change of the turbidity value compared to reference value will thus indicate the presence of gas in the liquid.

Preferably the reference value, as soon as it is determined, is compared with a threshold. A self-monitoring of the device is obtained from this comparison, with the aid of which contaminations or device outages can be detected. If at ambient pressure a turbidity of the liquid by comparing the reference value with the threshold is established, this especially indicates a marked contamination of the measurement apparatus. With a predefined threshold the limit value can be formed by the threshold or can be a function of the threshold (e.g. the limit value corresponds to 80% of the threshold). In normal circumstances the reference value lies below the limit value, i.e. the liquid is "clear" at ambient pressure or system pressure.

As an alternative to the predetermined numerical value for the threshold, the threshold is calculated in accordance with a further preferred variant on the basis of the measured reference value. In order to form the threshold a tolerance range Δ is especially added to the reference value here, through which an increase in the turbidity is quantitatively expressed. If the turbidity value exceeds the reference value by the tolerance range Δ (i.e. if the turbidity value reaches the threshold and is greater than the threshold), a turbidity of the liquid is present.

To determine the turbidity value it is preferred that an intensity of the measurement signal after coming into contact with the liquid in the measurement cell be included. The more intensive the turbidity, the greater is the quantity of gas in the liquid.

In accordance with a preferred variant a portion of the wave-shaped measurement signal transmitted through the liquid is measured by the detector being disposed such that the measurement cell is located between the measurement signal transmitter and the detector. In accordance with an alternate variant a portion of the measurement signal reflected by the liquid is measured by the detector being disposed on the side of the measurement cell had which the measurement signal transmitter is also located. Measurement systems are also possible in which both the transmitted and also the reflected measurement signal are measured. In such cases account is taken of the fact that gas bubbles within the liquid reduce the intensity of the light passing through the liquid and thus increase the proportion of the scattered measurement signal, so that the turbidity value increases. An ageing of the measurement signal transmitter as well is the contamination of the transparent measurement cell weakens the intensity of the waves passing through and thus of the measurement signal and of the scattered measurement signal, i.e. the turbidity value remains constant.

With a view to a trouble-free measurement a speed of the liquid is regulated such that gas bubbles are flushed away from a wall of the measurement cell. Through this an unfavorable influencing of the measurement results, especially during a continuous passage of sub-quantities of the liquid through the measurement cell, is avoided.

BRIEF DESCRIPTION OF THE SEVERAL VIEWS OF THE DRAWING

An exemplary embodiment of the invention is explained in greater detail on the basis of the drawing, in which.

DESCRIPTION OF THE INVENTION

Figure 1:
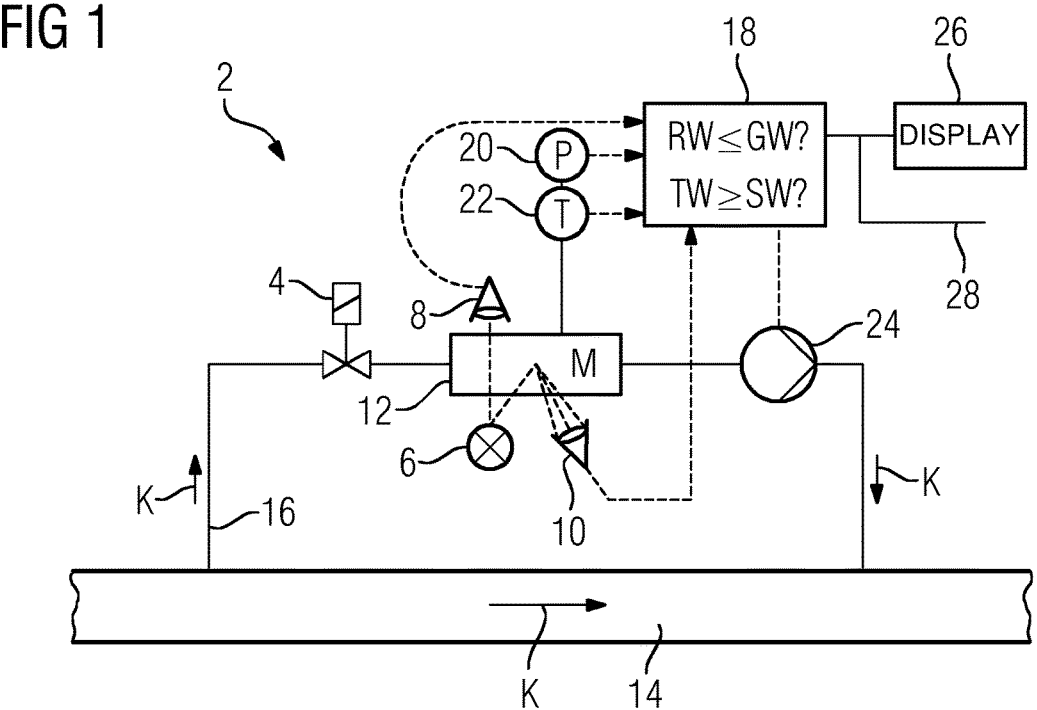
FIG. 1 shows a device for discontinuous monitoring of the gas content of a coolant of a fuel cell.

The same reference characters have the same meaning in the different figures.

FIG. 1 shows a first device 2 for measuring the gas content of a liquid coolant K, here cooling water for a fuel cell not shown in any greater detail. The device 2 comprises an inlet valve 4, a measurement signal transmitter 6 for a wave-shaped measurement signal, which is a light source in the exemplary embodiment shown, two detectors 8, 10 which are shown symbolically as open eyes, and also a measurement cell 12 transparent for light of the light source 6. Suitable light sources 6 are LEDs, incandescent lamps, gas discharge lamps etc. Each of the light detectors can comprise photo transistors, photodiodes or photo resistors for example.

As an alternative to light measurement the measurement signal transmitter 6 can be an ultrasound transmitter not shown in any greater detail here, the detector 8, 10 then accordingly being an ultrasound detector.

In the exemplary embodiment shown, with the aid of the light detectors 8, 10, a light from the light source 6 is measured after coming into contact with the cooling water K in the measurement cell 12. A first light detector 8 in this case is provided for measurement of the light transmitted through the cooling water K in the measurement cell 12 and is disposed in this case such that the measurement cell 12 is located between it and the light source 6. A second light detector 10 is disposed on the same side of the measurement cell 12 as the light source 6 and in this case measures the light reflected from the sub-quantity M on the cooling water K.

The device 2 is assigned in parallel to a main line 14 for the cooling water K. In the open state of the inlet valve 4 a sub-quantity M of cooling water K is conveyed via the ancillary line 16 from the main line 14 into the measurement cell 12. When the measurement cell 12 is especially completely filled up with cooling water K the inlet valve 4 is closed. Subsequently a reference measurement is carried out, in which a reference value RW for the turbidity of the cooling water K is obtained. A change of the transmission or reflection behavior of the liquid as a result of the formation of gas bubbles in the measurement cell is referred to as turbidity here. The reference value RW is stored in an analysis and control unit 18 which is likewise part of the device 2. In the exemplary embodiment shown only one unit is provided for analysis of the measurement results and for controlling the components of the device 2, as an alternative two separate units can also assume these two functions.

In order to minimize the influence of colorations or contaminations in the cooling water K or the influence of an ageing or attenuation of the light source 6 on the measurement or even to suppress it, the reference value RW is compared in the analysis and control unit 18 with a predetermined, fixed limit value GW. If the reference values RW corresponds to the limit value GW or exceeds said value, the functionality of the device 2 is checked. In this way a self-monitoring of the device 2 takes place, in which contaminations or device outages are recognized at an early stage. Normally the reference value RW is smaller than the limit value GW, then the cooling water K is clear enough to carry out the measurement.

After the reference measurement a pressure $p_m$ is lowered in the measurement cell 12. The pressure $p_m$ and also the temperature $T_m$ in the measurement cell 12 are monitored, in this case with the aid of a pressure sensor 20 and the temperature sensor 22. If the cooling water K contains dissolved gas, this gas occurs in the expansion of the cooling water K in the measurement cell 12 in the form of small bubbles, which lead to a turbidity of the cooling water K. Since however the cooling water K, on reaching the boiling point (boiling pressure and boiling temperature) itself vaporizes in the form of small bubbles, which influence the measurement results for the turbidity, the pressure $p_m$ and if necessary the temperature $T_m$ are regulated in the measurement cell 12 such that they constantly remain above the boiling point, especially at least 50 mbar above the boiling point.

On the basis of the light measurement in a vacuum, a turbidity value TW for the cooling water K in the measurement cell 12 is determined. For determining the turbidity value TW it is sufficient for only one light detector 8, 10 to be provided, which detects either the light let through or the reflected light. For determining the turbidity value TW in particular the intensity of the light after it has come into contact with the cooling water K in the measurement cell 12 is included.

The determined turbidity value TW is supplied to the analysis and control unit 18 and compared with a threshold SW. The threshold SW can be predetermined as a numerical value, as an alternative however the threshold SW can be defined for a specific measurement in that it is dependent on the reference value RW. If the turbidity value TW remains within a predetermined tolerance range and does not reach the threshold SW, it can be concluded from this that no gas bubbles are contained in the cooling water K. In this case the sub-quantity M of cooling water K, which was measured in the measurement cell 12, is fed back via a pump 24 into the main flow line 14. The pump 24 is especially controlled by the analysis and control unit 18.

If however the turbidity value TW reaches the threshold SW or exceeds said threshold, then this is a sign that gas is contained in the cooling water K. To obtain information about the quantity of gas contained in the cooling water K, account is taken in such cases of the pressure $p_m$ and the temperature $T_m$ at which the turbidity of the cooling water K occurs in the measurement cell 12. The display 26 can be used in such cases to display the proportion of gas in the cooling water K. In addition to this the result of the comparison of the turbidity value TW with the threshold SW can also be displayed in the display 26. For detected gas in the cooling water K, i.e. for an occurrence of a turbidity in the measurement cell 12, a control signal 28 is also output which causes a degassing device, especially a vacuum degasser not shown in any greater detail here, disposed downstream of the device 2, to be activated. In this case, after the measurement in the measurement cell 12, the sub-quantity M of cooling water K is subsequently processed in the vacuum degasser.

Figure 2:
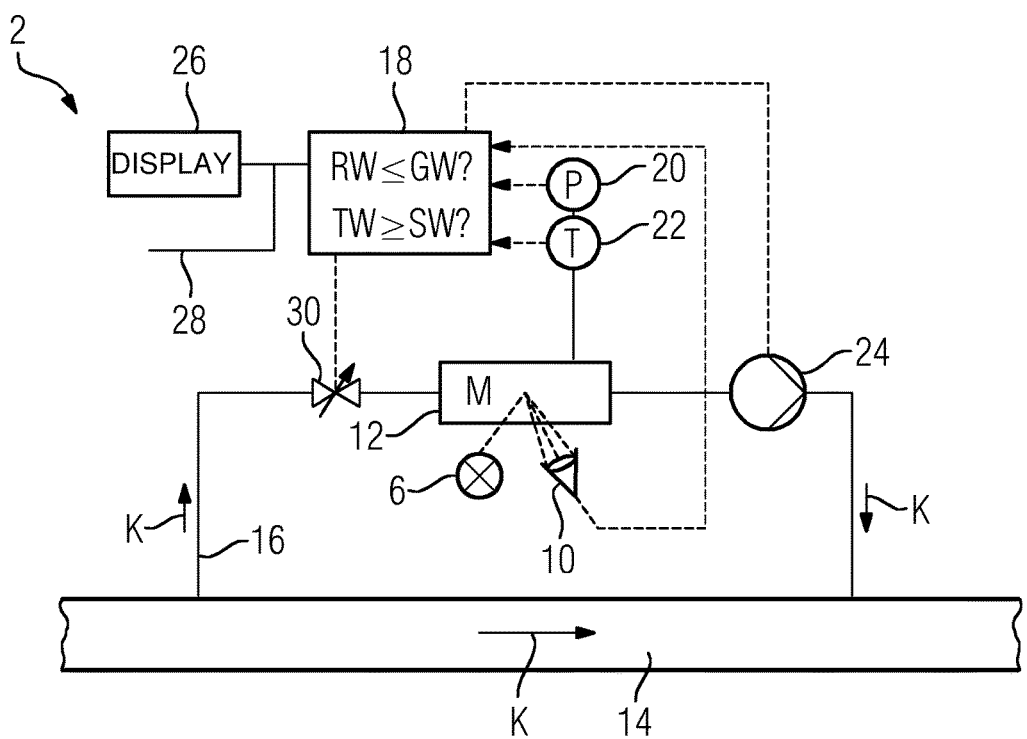
FIG. 2 shows a device for continuous monitoring of the gas content of a coolant of a fuel cell.

The device 2 for monitoring the gas content in the cooling water K in accordance with FIG. 2 differs from the device 2 in accordance with FIG. 1 essentially in that the arrangement in the second exemplary embodiment is suitable for a continuous measurement. For this the inlet valve 4 is replaced by a regulation valve 30. The regulation valve 30 is activated by the analysis and control unit 18 in order to regulate the inflow of cooling water K into the measurement cell 12. At a constant speed of the pump 24 the regulation valve 30 is closed slowly. In this case the pressure $p_m$ falls in the measurement cell 12 until gas bubbles form. The limit for the measurement of the gas content in the sub-quantity M lies in this case at around 50 mbar above the boiling pressure. It can thus be established from the occurrence of a turbidity in the measurement cell 12 in the measurement area whether gas is contained in the cooling water K. Through the further evaluation of the pressure $p_m$ and the temperature $T_m$ at the onset of the turbidity the gas content can also be measured.

Figure 3:
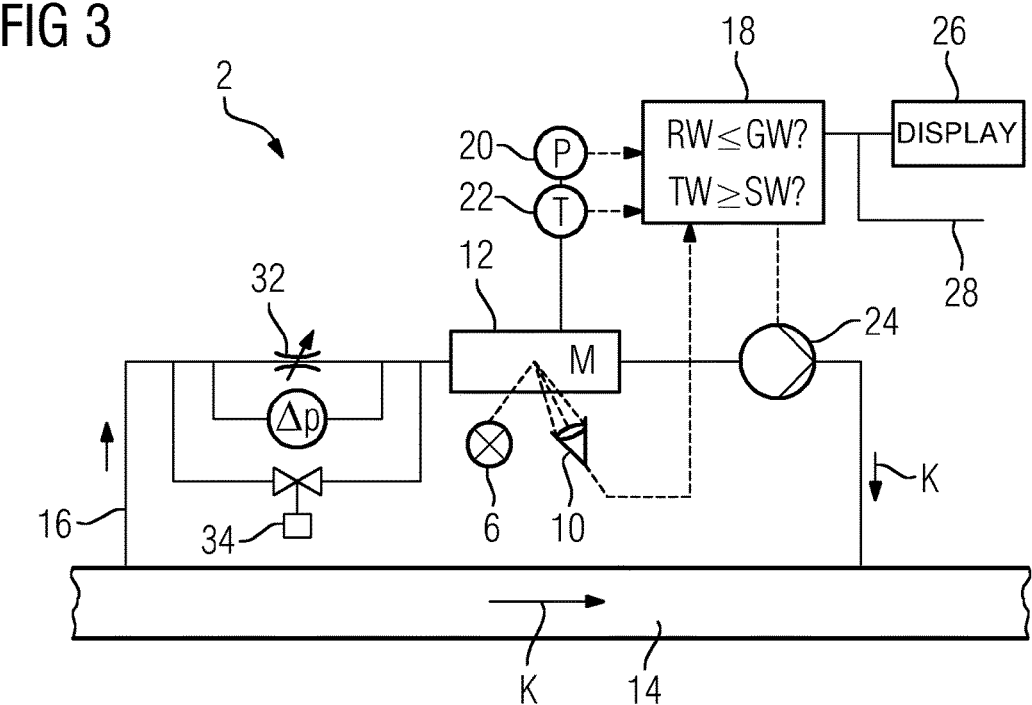
FIG. 3 shows a third embodiment variant of a device for measuring the proportion of gas in a liquid.

In accordance with FIG. 3 the cooling water K flows through a fixed choke valve 32 into the measurement cell 12. The pump speed is changed so that an ever lower pressure is set in the measurement cell 12 until turbidity occurs. The measurement begins if in particular a pressure difference of at least 100 mbar occurs via the choke valve 32.

In all the figures shown the turbidity value TW is measured with the aid of a sub-quantity M of cooling water K, which is diverted through the ancillary line 16. As an alternative the device 2 for monitoring the gas content in the cooling water K can be integrated directly into the main line 14, so that the entire coolant flow is directed through the device 2 for measurement purposes.

The measurement is started as a rule at a differential pressure of approximately 100 bar below the start pressure.

In addition, in all versions shown, a flushing valve 34 with a large diameter is provided before the measurement cell 12, which is only shown in FIG. 3. If gas bubbles have attached themselves to the wall of the measurement cell 12, these are flushed away with the aid of the flushing valve 34, which allows a large throughflow. A falsification of the measurement results is thus avoided.

Figure 4:
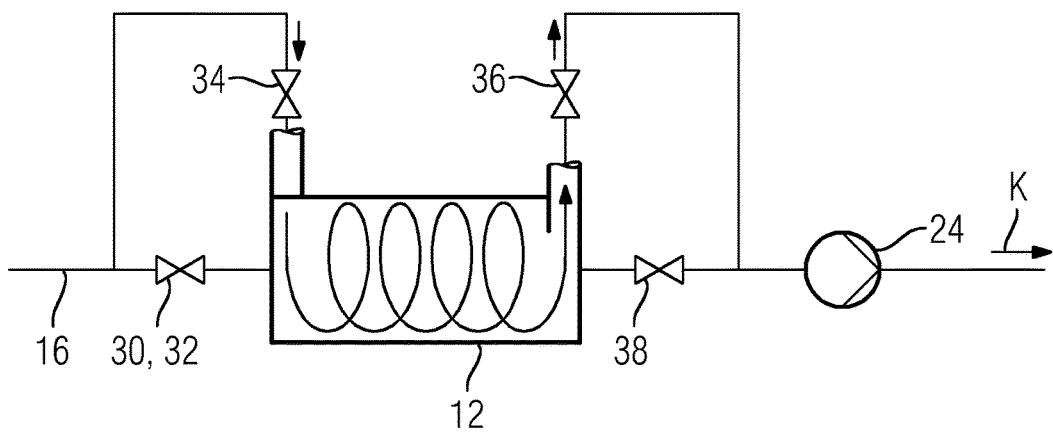
FIG. 4 shows an arrangement of a measurement cell.

The flushing out of the measurement cell 12 is explained in detail with reference to FIG. 4. The measurement cell 12 is supplemented by two connections which create a flow within the measurement cell 12, which winds itself in the shape of a screw around the central axis. This can be achieved if the connections for the flushing cycle are arranged radially, as shown in FIG. 4. To this end, as well as the flushing valve 34 already considered, two further valves 36, 38 are required, which switch over between flushing and measurement.

For the measurement the flushing valve 34 or 36 is closed and the valve 38 opened. This produces an axial flow through the measurement cell 12.

To cleanse the walls of bubbles adhering to them the flushing valves 34 and 36 are opened, valve 38 is closed and a rotary flow is produced. Through the rotation of the measurement cell content a higher flow speed on the wall is achieved than if the measurement cell 12 were to have an axial flow flowing through it with the same valve diameters. Bubbles are flushed away better by this. Small diameters can then be used for flushing valves 34, 36 with a radial throughflow than with an axial throughflow of the measurement cell 12. As an alternative the flushing valve 34 could be replaced by a choke valve or a regulation valve.

The invention claimed is:

1. A method of measuring a gas content in a liquid, the method which comprises:
   conveying at least one sub-quantity of the liquid into a measurement cell;
   setting a vacuum in the measurement cell;
   subjecting the sub-quantity to a measurement signal selected from the group consisting of acoustic signals and electromagnetic wave signals;
   measuring the measurement signal after coming into contact with the sub-quantity;
   determining a turbidity value of the liquid and comparing the turbidity value with a threshold;
   if the turbidity value is greater than or equal to the threshold, measuring a pressure and a temperature in the measurement cell; and
   determining the gas content in the liquid based on stored characteristic data for a solubility of the gas in the liquid as a function of the pressure and the temperature.

2. The method according to claim 1, wherein said measurement signal is an electromagnetic wave signal in the form of a visible light signal.

3. The method according to claim 1, wherein said measurement signal is an acoustic measurement signal.

4. The method according to claim 3, which comprises subjecting the sub-quantity to an acoustic measurement signal in the form of ultrasound.

5. The method according to claim 1, which comprises controlling one or both of the pressure and the temperature in the measurement cell to remain above a boiling point of the liquid.

6. The method according to claim 1, wherein the threshold is specified as a numerical value.

7. The method according to claim 1, which comprises, prior to setting the vacuum, carrying out a measurement with the measurement signal for defining a reference value.

8. The method according to claim 7, which comprises comparing the reference value with a threshold.

9. The method according to claim 7, which comprises computing the threshold on a basis of the reference value.

10. The method according to claim 1, which comprises using an intensity of the measurement signal after coming into contact with the liquid in the measurement cell to determine the turbidity value.

11. The method according to claim 1, which comprises measuring a proportion of the measurement signal transmitted through the liquid.

12. The method according to claim 1, which comprises measuring a proportion of the measurement signal reflected by the liquid.

13. The method according to claim 1, which comprises controlling a flow speed of the liquid such that gas bubbles are flushed away from a wall of the measurement cell.

14. A device for measuring a gas content in a liquid, the device comprising:
    a transparent measurement cell for receiving at least a sub-quantity of the liquid;
    a vacuum system for generating a vacuum in the measurement cell;
    a measurement signal emitter for applying a measurement signal selected from the group consisting of acoustic signals and electromagnetic wave signals to the sub-quantity;
    at least one detector for measuring the measurement signal after coming into contact with the sub-quantity in the measurement cell;
    sensors for determining a pressure and a temperature in the measurement cell; and
    an analysis and control unit configured to determine a turbidity value of the liquid and to compare the turbidity value with a threshold and, if the turbidity value is greater than or equal to a threshold, to determine the gas content in the liquid on a basis of stored characteristic data for the solubility of the gas in the liquid as a function of the pressure and the temperature.

15. In combination with an electrochemical cell, the device according to claim 14 for measuring a gas content in a coolant of the electrochemical cell.

16. The combination according to claim 15, wherein the electrochemical cell is a fuel cell.

* * * * *